(12) United States Patent
Madaus et al.

(10) Patent No.: US 8,286,634 B2
(45) Date of Patent: *Oct. 16, 2012

(54) HOLDING DEVICE FOR A RESPIRATORY MASK

(75) Inventors: Stefan Rolf Madaus, Krailling (DE); Harald Wolfgang Vögele, Gauting (DE)

(73) Assignee: MAP Medizin Technologie GmbH, Martinsried (DE)

( * ) Notice: Subject to any disclaimer, the term of this patent is extended or adjusted under 35 U.S.C. 154(b) by 1355 days.

This patent is subject to a terminal disclaimer.

(21) Appl. No.: 11/529,296

(22) Filed: Sep. 29, 2006

(65) Prior Publication Data

US 2007/0017525 A1    Jan. 25, 2007

Related U.S. Application Data

(62) Division of application No. 10/333,020, filed on Jun. 2, 2003, now Pat. No. 7,562,658.

(30) Foreign Application Priority Data

Jul. 21, 2000  (DE) .................................. 100 35 946
Jun. 22, 2001  (WO) ........................ PCT/EP01/07132

(51) Int. Cl.
*A62B 18/02* (2006.01)
*A62B 7/10* (2006.01)
*A62B 18/08* (2006.01)
*A62B 9/04* (2006.01)
*A62B 9/06* (2006.01)
*A41D 13/00* (2006.01)
*A42B 1/18* (2006.01)

(52) U.S. Cl. ......... 128/207.11; 128/205.25; 128/206.18; 128/206.27; 128/207.13; 128/206.21; 128/202.27; 128/206.13; 128/206.14; 128/206.16; 128/206.23; 128/206.24; 128/207.17; 2/9; 2/206

(58) Field of Classification Search ............. 128/205.25, 128/206.18, 206.27, 207.11, 207.13, 206.21, 128/202.27, 206.13, 206.14, 206.16, 206.23, 128/206.24, 207.17; 2/206, 9

See application file for complete search history.

(56) References Cited

U.S. PATENT DOCUMENTS 2,016,210 A    10/1935   Mann
(Continued)

FOREIGN PATENT DOCUMENTS

DE    196 25 337    1/1998
(Continued)

OTHER PUBLICATIONS

International Search Report for PCT/EP01/07132, dated Nov. 6, 2001.

*Primary Examiner* — Patricia Bianco
*Assistant Examiner* — Nihir Patel
(74) *Attorney, Agent, or Firm* — Nixon & Vanderhye P.C.

(57) ABSTRACT

A holding device for a respiratory mask includes a headband adapted to extend in an application position from a forehead portion of a patient around a back head portion of the patient. A strengthening element is releasably coupled to the headband to add flexural strength to the headband. The strengthening element is adapted to extend from the forehead portion laterally to respective ear portions and to descend behind the respective ear portions towards the patient's neck. The strengthening element has bracket sections positioned below respective ear portions adjacent the back head portion. A support is coupled to respective bracket sections to support the bracket sections in the back head portion.

21 Claims, 6 Drawing Sheets

U.S. PATENT DOCUMENTS

| | | | |
|---|---|---|---|
| 2,259,817 A | 10/1941 | Hawkins | |
| 2,353,643 A | 7/1944 | Bulbulian | |
| 2,783,474 A | 3/1957 | Campagna et al. | |
| 3,234,940 A | 2/1966 | Morton, Jr. | |
| 3,752,157 A | 8/1973 | Malmin | |
| 3,792,702 A | 2/1974 | Delest | |
| 4,018,221 A | 4/1977 | Rennie | |
| 4,164,942 A * | 8/1979 | Beard et al. | 128/201.19 |
| 4,665,566 A | 5/1987 | Garrow | |
| 4,744,358 A | 5/1988 | McGinnis | |
| 4,774,946 A | 10/1988 | Ackerman et al. | |
| 4,821,736 A | 4/1989 | Watson | |
| 4,910,804 A | 3/1990 | Lidgren | |
| 5,570,689 A | 11/1996 | Starr et al. | |
| 5,687,715 A * | 11/1997 | Landis et al. | 128/207.18 |
| 6,205,590 B1 | 3/2001 | Gorman | |
| 6,332,465 B1 | 12/2001 | Xue et al. | |
| 6,470,886 B1 | 10/2002 | Jestrabek-Hart | |
| 6,494,207 B1 * | 12/2002 | Kwok | 128/207.11 |
| 6,565,461 B1 | 5/2003 | Zatlin | |
| 6,610,032 B1 | 8/2003 | Prody | |
| 6,712,072 B1 * | 3/2004 | Lang | 128/206.27 |
| 7,219,670 B2 * | 5/2007 | Jones et al. | 128/206.27 |
| 7,562,658 B2 * | 7/2009 | Madaus et al. | 128/207.17 |
| 2004/0025882 A1 | 2/2004 | Madaus et al. | |
| 2004/0065328 A1 * | 4/2004 | Amarasinghe et al. | 128/206.27 |

FOREIGN PATENT DOCUMENTS

| | | |
|---|---|---|
| DE | 29923126 | 5/1999 |
| EP | 0958841 | 11/1999 |

* cited by examiner

HOLDING DEVICE FOR A RESPIRATORY MASK

This application is a divisional of U.S. application Ser. No. 10/333,020, filed Jun. 2, 2003, pending, which is a National Phase of PCT/EP01/07132, filed Jun. 22, 2001, which claims priority to German Patent Application DE 100 35 946.9, filed Jul. 21, 2000, each of which is incorporated herein by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The present invention refers to a holding device for a respiratory mask, as it may for instance be used in the field of sleep medicine for fixing a nasal mask to the face of a patient.

2. Description of Related Art

Known holding devices of the above-mentioned kind usually comprise an upper belt arrangement and a lower belt arrangement, which are joined through a web arrangement arranged in the application position of the holding device at the back head portion of the patient. The two belt arrangements are made of a flexible textile material. In the area of the free end portions of the upper and lower belt arrangement, Velcro fastener means are provided through which the effective length and thus the press-on pressure of the respiratory mask against the face of the patient can be adjusted depending on the respective need. The upper belt arrangement may be connected in certain mask types with a forehead holding device so that the press-on pressure of the forehead rest element against the forehead of the patient can be defined by adjusting the effective length of the upper belt arrangement.

Depending on required therapeutic pressure of the respiratory gas supplied via the respiratory mask and depending on the individual face structure of the patient, mask press-on forces are partially required, which leave visible marks after a longer application of the mask on the face of the patient or in the forehead area.

BRIEF SUMMARY OF THE INVENTION

The invention is based on the object to provide a manageable holding device for a respiratory mask through which a desired respiratory mask press-on force by obtaining an improved wearing comfort can be exerted in a reliable manner.

Thereby it becomes possible in an advantageous manner to fix the respiratory mask at low tension forces on the face of the patient. For the case that e.g. due to an increased internal mask pressure, the mask tends to lift off the patient's face, a correspondingly greater mask fixing force is automatically exerted.

An extremely reliable fixing of the forehead rest element in the forehead portion of the patient is achieved in an advantageous manner without significant tensile forces being exerted on the belt arrangement extending across the forehead and the back of the head.

An embodiment that is especially advantageous in view of an especially high wearing comfort is given in that the upper belt arrangement is formed with a waist in a manner that it extends from the forehead portion to the respective ear portion of the patient, and then takes a course diverging in the area of the ears towards the parting, and directly behind the ears descends and encompasses the back head portion of the patient in the area of the neck or approximately on the level of the patient's nose.

The flexible insert provided in the holding device may for instance be made of a thermoplastic plastic material layer having a thickness of 0.8 to 1.5 mm. A pad support is arranged in an area provided between the tensile-rigid inset and the patient. This pad support is according to an especially preferred embodiment of the invention formed by a thin and locally stitched foam layer on whose outer side a web material is backed. This web material may be a textile material or for instance a washable material to be wet-cleaned.

The headband arrangement of the respiratory mask is preferably provided with an adjustment means through which the effective length of the headband can be adjusted variably. The adjustment means may also be formed by a lock/clamping shift mechanism and/or by a Velcro fastener means.

According to an especially preferred embodiment of the invention, the flexible layer is formed of a plastic material, e.g. of a thermoplastic plastic material. As an alternative hereto or in combination therewith, it is also possible to make the flexible layer of a metal material, e.g. of a thin spring steel sheet. The bending elasticity of the flexible layer may be affected in a defined way by punchings or deep drawing structures. The flexible layer is, according to an especially preferred embodiment of the invention, punched out of a corresponding web material by means of a punching process. As an alternative, it is also possible to make the flexible layer by means of a plastic shaping process, e.g. of a thermoplastic material in an injection tool. It is also possible to provide especially reinforcing or functional structures on the mask holding device.

According to an especially preferred embodiment of the invention, the flexible layer is made of a thermo-formable material. Thereby it becomes possible in an advantageous manner to adapt the headband heated to a temperature of 60° C. individually to the patient, wherein the headband after cooling to ambient temperature may keep an advantageous spatial shape in view of a possible low surface pressure.

An embodiment that is especially advantageous in view of an especially high wearing comfort is provided in that the headband section is provided with a padding means. The padding means may preferably be formed of an open-cell foamed foam material. The padding means is preferably provided with a textile or washable layer. By the formation of locally stitched sections, the padding behavior of the padding means may be adapted in an advantageous manner.

An embodiment of the invention that is especially advantageous in view of an especially reliable fixing of the respiratory mask on the headband is given in that the holding device is provided—at least section-wise—with one of the two complementary structures of a Velcro fastening means. For this purpose, the headband is formed in a multi-layered backed manner. Thus, the flexible layer possibly provided with breakthroughs may for instance form the core portion of the headband, wherein a padding and a cover layer chosen with respect to structure and color are backed on the side facing the head of the patient in the application position of the headband.

An embodiment that is advantageous in view of an especially high wearing comfort is given in that the headband section has, seen in application position, an extension directed from the forehead portion to the upper ear portion, and an extension locally drawn up in the ear portion, wherein the headband portion directly after the ear portion has an extension descending towards the back of the head.

The above-mentioned object is solved according to a further solution idea by a holding device for a respiratory mask, having an element of increased flexural strength extending from the forehead portion laterally to the upper ear portion, and a bracket section descending behind the ear towards the neck, and a means for supporting the bracket section in the back head portion.

Thus, it becomes possible in an advantageous manner to apply a respiratory mask in a comfortable manner and possibly to refrain from using a belt arrangement.

The element of increased flexural strength may for instance be made of a wire material, in particular of a spring steel material. In an advantageous manner the element of increased flexural strength has a section projecting towards the nose tip of the patient that urges the respiratory mask against the face of the patient.

The introduction of forces into the respiratory mask is preferably implemented in that a deformation axis extends through a point of gravity of the mask support surface.

The support on the back of the head is preferably implemented by a padded band element in a manner that a deformation axis is defined which basically corresponds to the deformation axis acting on the mask.

BRIEF DESCRIPTION OF THE SEVERAL VIEWS OF THE DRAWING(S)

Further details can be derived from the following description in connection with the drawing.

DETAILED DESCRIPTION OF ILLUSTRATED EMBODIMENTS

Figure 1:
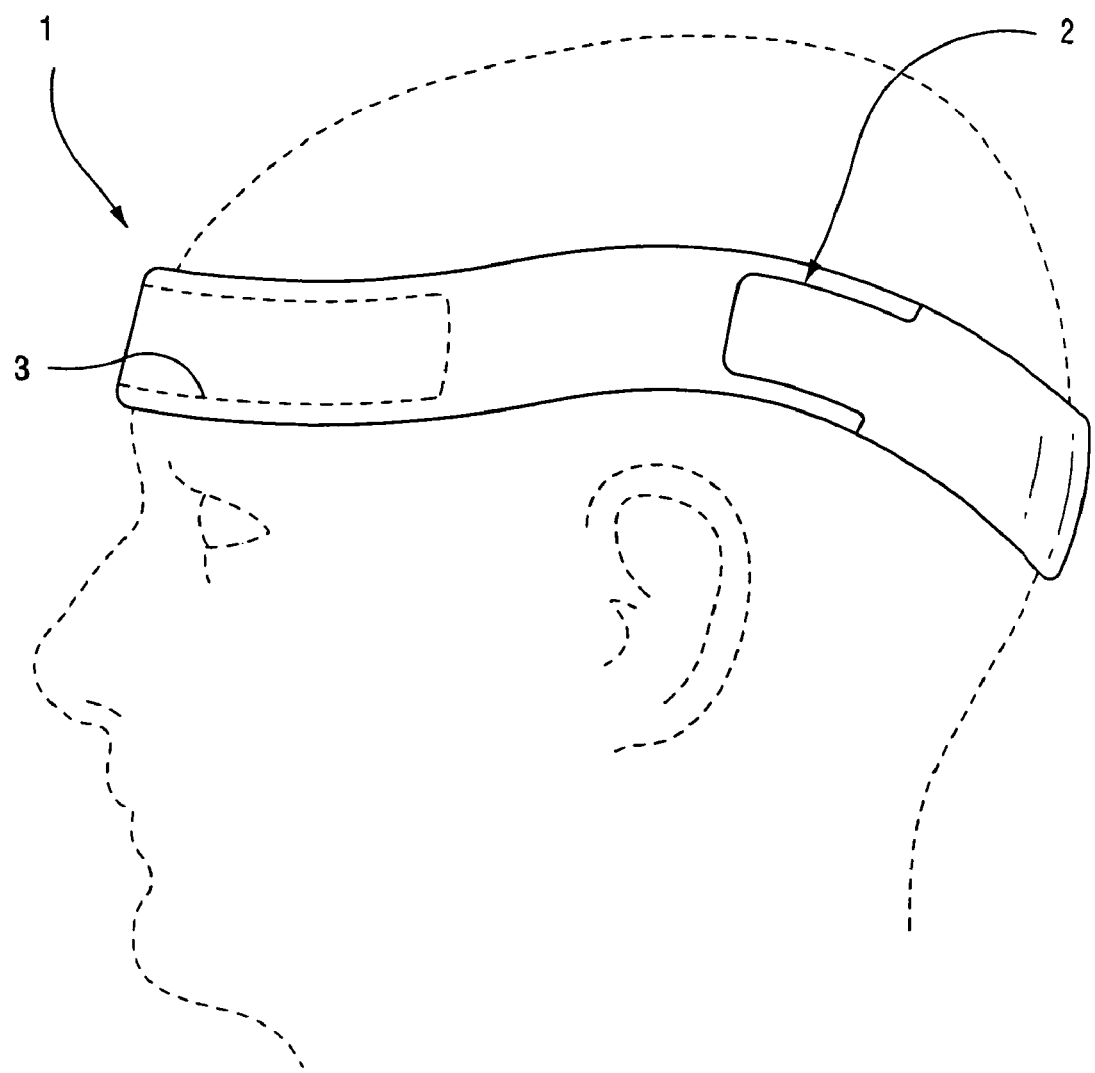
FIG. 1 shows a simplified view to explain the application position of a holding device for a respiratory mask according to a first preferred embodiment of the invention.

FIG. 1 shows a first preferred embodiment of a holding device for a respiratory mask, which comprises a headband section 1, which is laterally reinforced by a layer flexible in the winding direction. The headband section 1 extends in the application position from the forehead portion of the patient around the back head portion of the patient. To adapt the effective length of the headband section 1 to the individual head circumference of the patient, an adjustment means 2 is provided, which in the embodiment shown is formed by a Velcro fastener means. The outer portion of the headband section 1 visible in this case is formed by a fleece material, which can be brought into an adhesive connection with corresponding complementary Velcro fastener structures. Thus, it becomes possible, in particular in the area indicated by the dotted lines 3 to fix a forehead rest element of a respiratory mask. It is possible by the flexible layer integrated into the headband to give the headband an arbitrary extension in the lateral direction. In the embodiment shown in this case, the headband extends from the front forehead portion towards the upper ear portion and above the ear it has an extension diverging towards the top. In its further extension towards the back head portion, the headband descends towards the neck.

Figure 2:
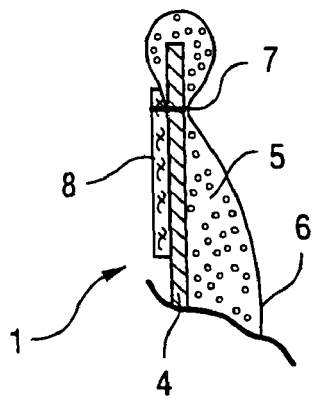
FIG. 2 shows a simplified sectional view to explain a preferred internal structure of a holding device for a respiratory mask with a flexible inset that is has lateral flexural strength.

FIG. 2 shows a simplified sectional view through a section of the headband 1.

The headband 1 has a reinforcement layer 4 (also referred to as a reinforcement insert) which is formed in this case of a thermoplastic material, the thickness of the reinforcement insert being in this case 0.75 mm. On the side of the reinforcement insert 4 facing the patient in the application position, a padding 5 is provided, which in this case is formed of an open-cell foamed foam material. The padding 5 in turn is covered by a cover layer 6 which is formed in this case by a textile material. The cover layer 6 and the padding 5 are coupled via a connection point 7 with the flexible layer. The connection point 7 is in this case formed by a stitching seam.

The padding 5 and a section of the cover layer are guided around a lateral edge of the reinforcement layer 4. This leads to an especially advantageous padding of the lateral edge of the reinforcement insert 4. The section guided around the reinforcement insert 4 is sewed onto the reinforcement insert 4 by means of said stitching seam. The stitching seam extends in the embodiment shown through a fleece material 8, which points towards the outside in the application position of the headband. The fleece material 8 is additionally directly adhered onto the reinforcement insert 4.

Figure 3:
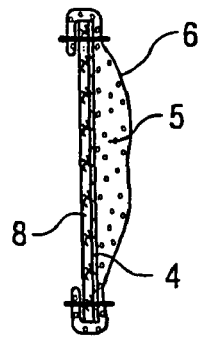
FIG. 3 shows a further, simplified sectional view to explain the inner structure of a further preferred embodiment of the holding device for a respiratory mask, also having a flexible insert.

FIG. 3 shows a further embodiment of the headband. Here, the padding body 5 is backed onto the reinforcement insert during a flame backing process. A fleece material layer 8 is provided on the rear side of the reinforcement insert 4 similar to the embodiment according to FIG. 2. The fleece material layer 8 is formed with respect to its layer thickness in a manner that a sufficient padding effect is achieved also towards the outside due to the fleece material layer 8. If needed, a padding may also be provided between the fleece material layer 8 and the reinforcement insert 4. In the embodiment shown in FIG. 3, the lateral edges of the reinforcement insert 4 are also lined by the material of a cover layer, which is guided around the lateral edges of the reinforcement insert and which is fixed by stitching seams.

Figure 4:
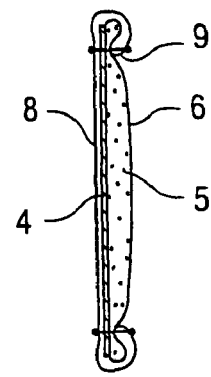
FIG. 4 shows a simplified sectional view through a holding device for a respiratory mask according to a fourth preferred embodiment having a padded circumferential edge stitched by a stitching seam.

The embodiment of the headband shown in FIG. 4 also comprises a reinforcement insert 4 and a fleece material layer 8 provided on the outwardly pointing side of the headband, said fleece material layer being guided around the lateral edge portion of the reinforcement insert 4 and which is fixed on the sides of the padding 5 together with a cover layer 6. The fixing is made preferably by stitching seams 9 that are shown in a highly magnified manner.

Figure 5:
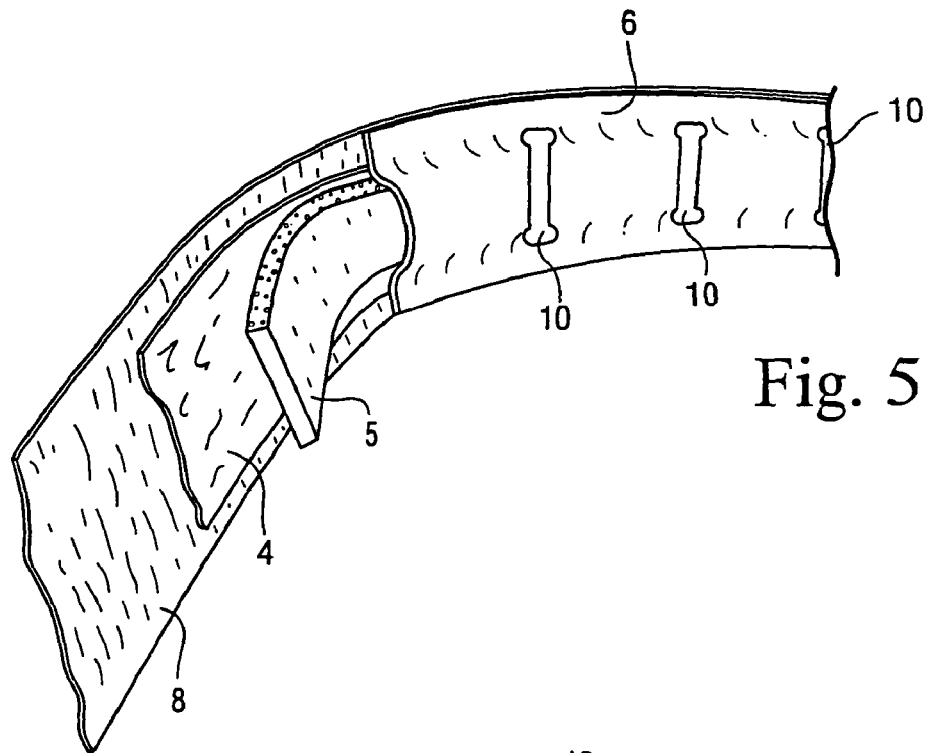
FIG. 5 shows a perspective view of a section of a holding device for a respiratory mask with a flexible inset that has flexural strength in the lateral direction and that has an integrated padding means.

FIG. 5 shows in a partially broken-up view a section of a headband according to the invention. The headband shown in this Figure again comprises a flexible reinforcement insert 4, which reinforces the headband against a bending around an axis perpendicularly to the headband rest surface. The flexible layer 4 is embedded between the rear cover layer, which is formed e.g. by the fleece material 8, and the inner cover layer 6 by interposition of the padding body 5. Stitching points 10 can be formed preferably by a thermo-welding process on the inner side of the headband, said stitching points providing the padding with a certain pre-load. The stitching points can for instance be formed during an ultrasonic welding process or by a correspondingly heated punching tool. An embodiment of the headband that is especially inexpensive to manufacture is provided in that the two layers 6, 8, and possibly also the reinforcement insert 4, are also connected to one another by an adhesion process.

Figure 6:
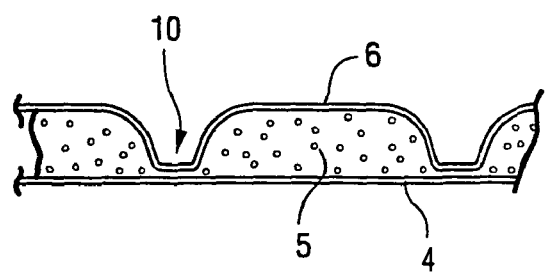
FIG. 6 shows a simplified detail sectional view to explain the stitching points formed by a melt-welding process on the inner side of the headband of the holding device.

A preferred embodiment of the stitching sections is shown in FIG. 6. As can be recognized, the cover layer 6 is welded onto the reinforcement layer 4 in the area of the welding points 10 through the hot-molten material of the padding 5.

Figure 7:
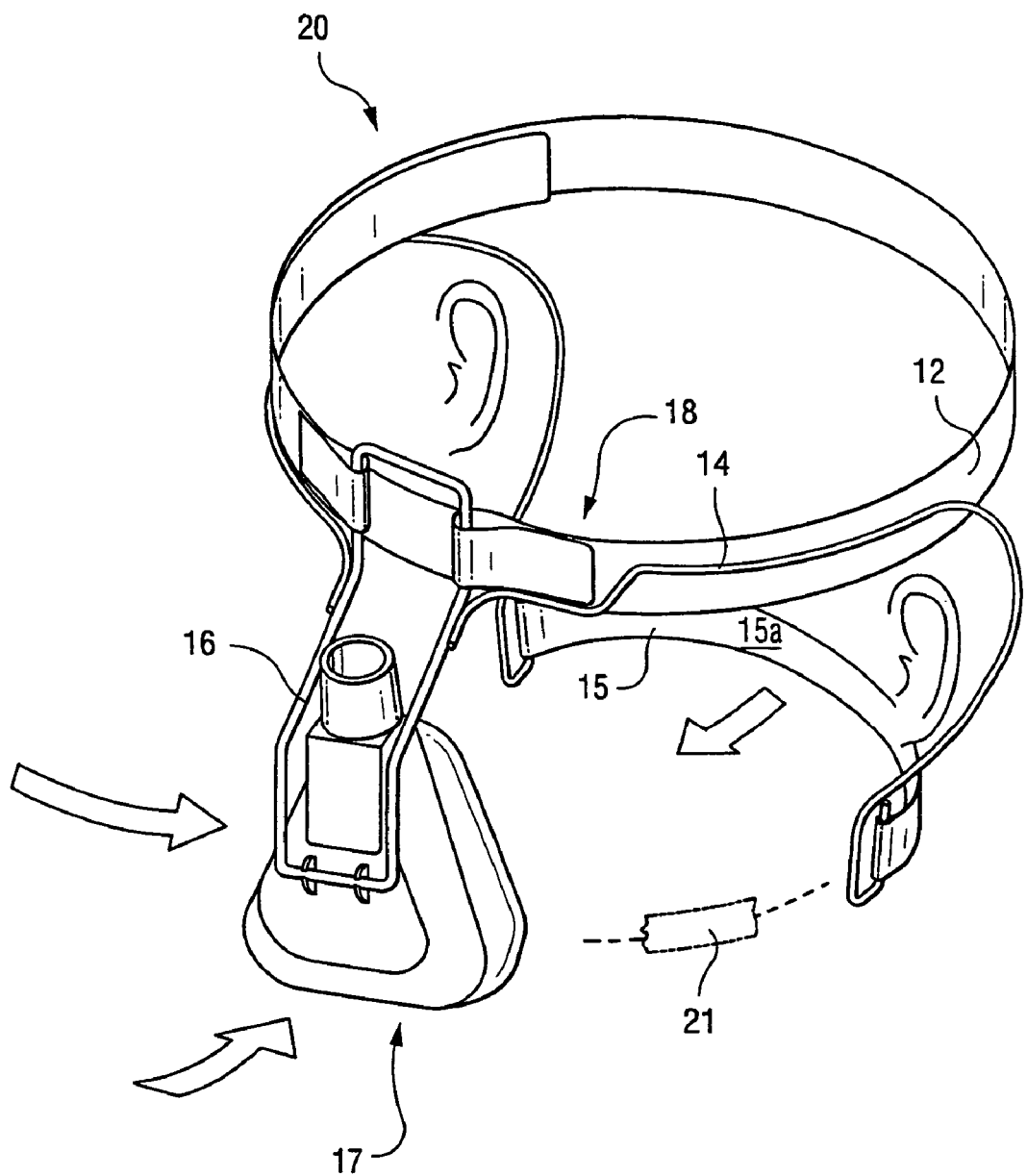
FIG. 7 shows a perspective view of a further embodiment of a holding device for a respiratory mask, in this case with a bracket element for exerting a respiratory mask press-on force.

FIG. 7 shows a further preferred embodiment of a holding device (also referred to as a holding arrangement) for a respiratory mask, which in this Figure comprises a headband 12, which is preferably in the same manner as the above-described headband 1 provided with an integral reinforcement layer. The headband 12 is provided with an element 14 having flexural strength (also referred to as a strengthening element or a reinforcement element), which extends in the application position of the holding device in a bracket-like descending manner behind the ear of the patient towards the neck portion. The element 14 having flexural strength may be supported via a support means 15 at the back head or neck portion of the patient. In the embodiment of the invention shown, the support means 15 is formed by a band element 15a that is longitudinally adjustable, which is coupled below the ear portion of the patient with the element 14 having flexural strength. A mask fixing means 16 (also referred to as a fixing element or a support frame) is provided on the element 14 having flexural strength, said mask fixing means extending from the forehead portion to the nose tip of the patient. The mask fixing means 16 is coupled with a respiratory mask 17 (e.g., nasal-only mask or nasal-only seal) in a section which basically extends in the area of the point of gravity that extends through the sealing pad of the facial rest zone defined by the respiratory mask. In the embodiment shown, the coupling of the respiratory mask 17 with the mask fixing means 16 is implemented in that the respiratory mask can be tilted to a certain extent. The arrangement is preferably adapted so that the deformation axis of the press-on force acting on the respiratory mask 17 substantially corresponds to the deformation axis caused by the support means and the headband 12 themselves.

The element 14 having flexural strength is preferably releasably fixed to the headband 12 via a Velcro fastener means 18.

The mask fixing means 16 and the element 14 having flexural strength are made of a steel spring wire in the embodiment shown in this case.

The headband 12 further comprises quick acting closure means 20 through which the headband 12 can be expanded and shortened in a defined manner. In the embodiment shown it is possible to attach a further band element 21 (indicated in dashed lines) to the element 14 having flexural strength, by means of which said band element additional holding forces can be exerted in the fashion of a belt arrangement onto the respiratory mask 17.

Figure 8:
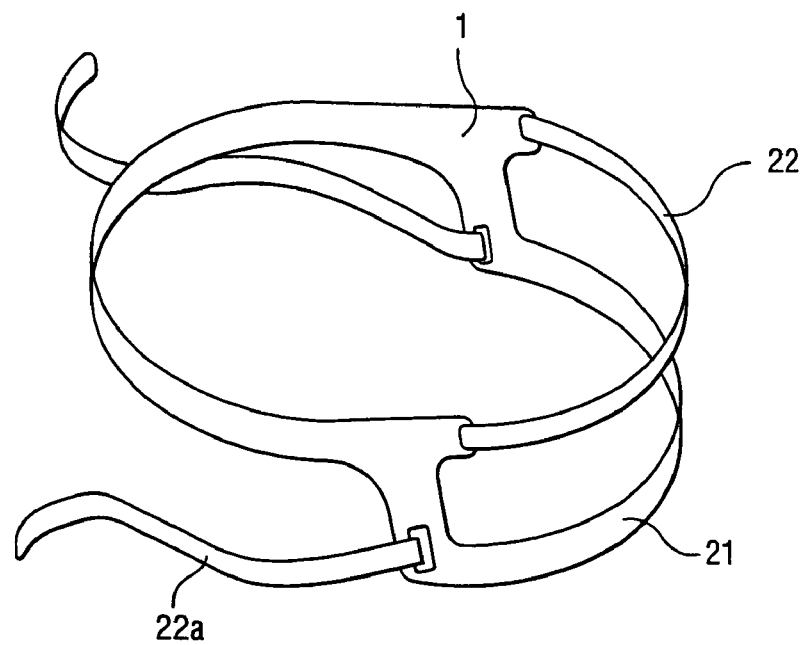
FIG. 8 shows a simplified perspective view of a further embodiment of a holding device for a respiratory mask having a reinforcement insert.

FIG. 8 shows a further embodiment of a holding device for a respiratory mask, which in turn comprises a headband 1, which is provided in the application surface with a substantially lateral reinforcement insert 4 which is of flexural strength and can be unwound in the circumferential direction. The headband 1 comprises in the application position behind the ear portion of the patient descending sections subsequently extending around the neck portion. An elastic band 22 is provided to fix the headband 1, said band extending around the back head portion of the patient. On the section of the headband 1 resting in the application position on the forehead of the patient, a forehead rest element of a respiratory mask arrangement may be fixed via a Velcro fastener means. Further forces may be exerted onto the respiratory mask via further lower belts 21, 22a.

Figure 9:
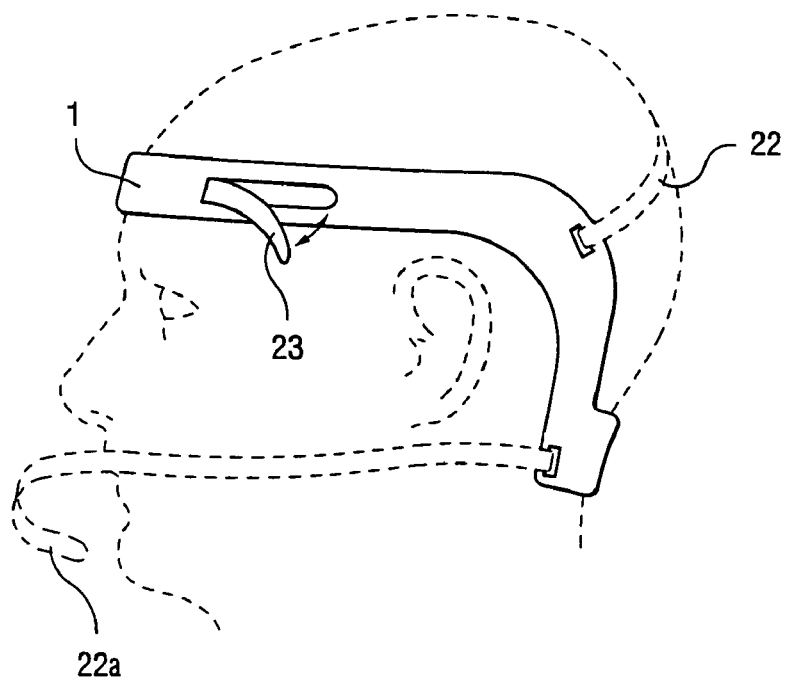
FIG. 9 shows a simplified view of the holding device, however basically with integrated forehead rest attachment flaps according to FIG. 8 in application position.

FIG. 9 shows as an example a holding means for a respiratory mask in the application position, the structure thereof basically corresponding to the holding device shown in FIG. 8. The holding device 1 extends from the forehead portion of the patient towards its upper ear portion and directly descends behind the ears of the patient towards the patient's neck. A respiratory mask (not shown in detail) may additionally be fixed via the lower belt arrangement 22a. By fixing the respiratory mask via the forehead rest element and the lower belt arrangement, an application of the respiratory mask advantageous in terms of ergonomics is obtained. The forehead support element of the respiratory mask (not shown) may be implemented via a Velcro fastener 23 shown in a simplified manner.

Figure 10:
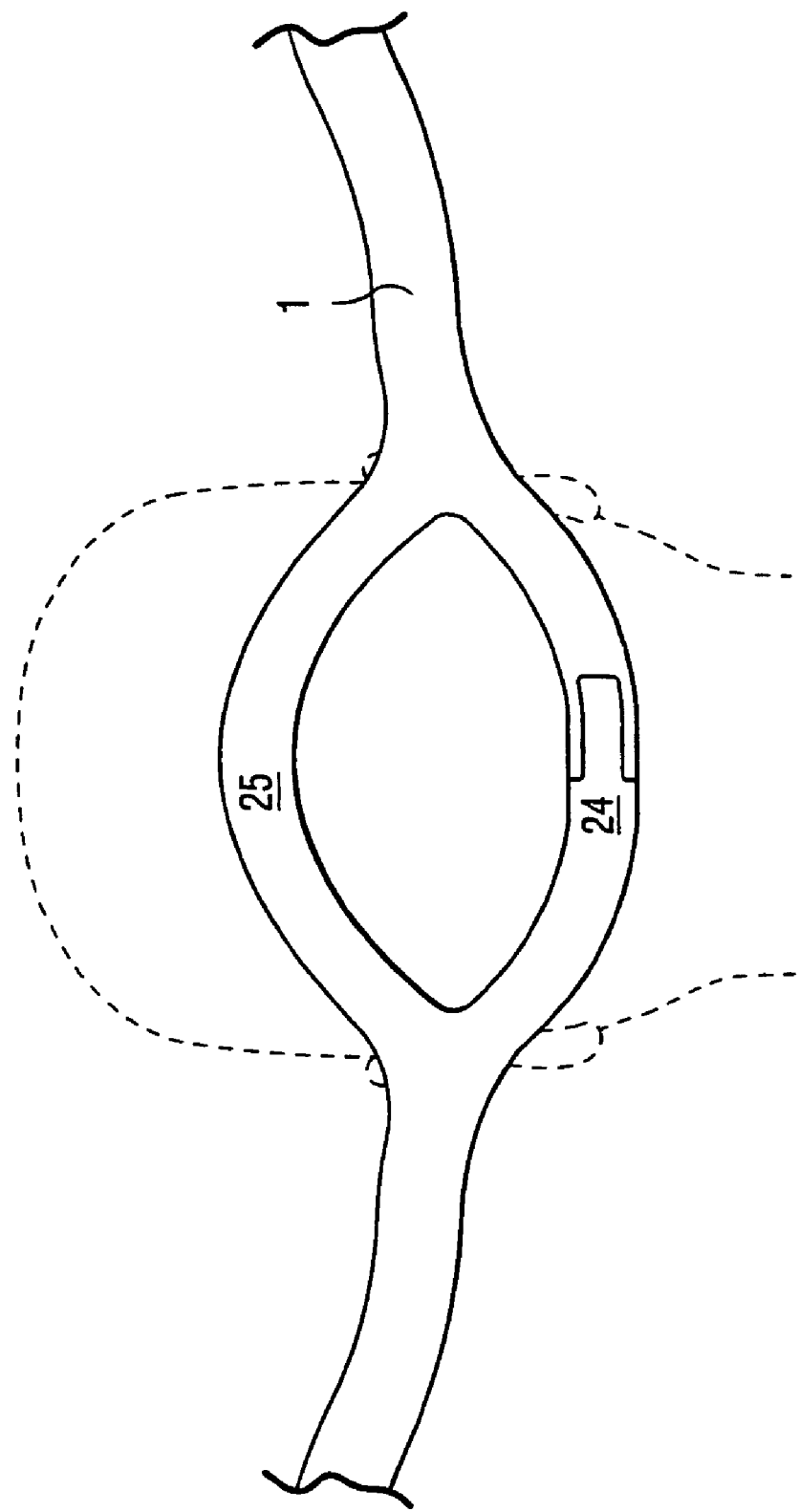
FIG. 10 shows a simplified view to explain a further embodiment of a holding device of a respiratory mask with a flexible reinforcement insert and an opening shown in this Figure in application position in the back head portion.

Instead of the elastic tension 22 provided in the embodiment according to FIG. 8, it is also possible to design the holding device 1 in a manner that this holding device defines in the back head portion of the patient a larger opening and is supported via at least two back head sections 25, 24 in the back head portion of the patient as shown in FIG. 10. The back head sections 25, 24 are preferably, as shown, adjustable in length.

Figure 11:
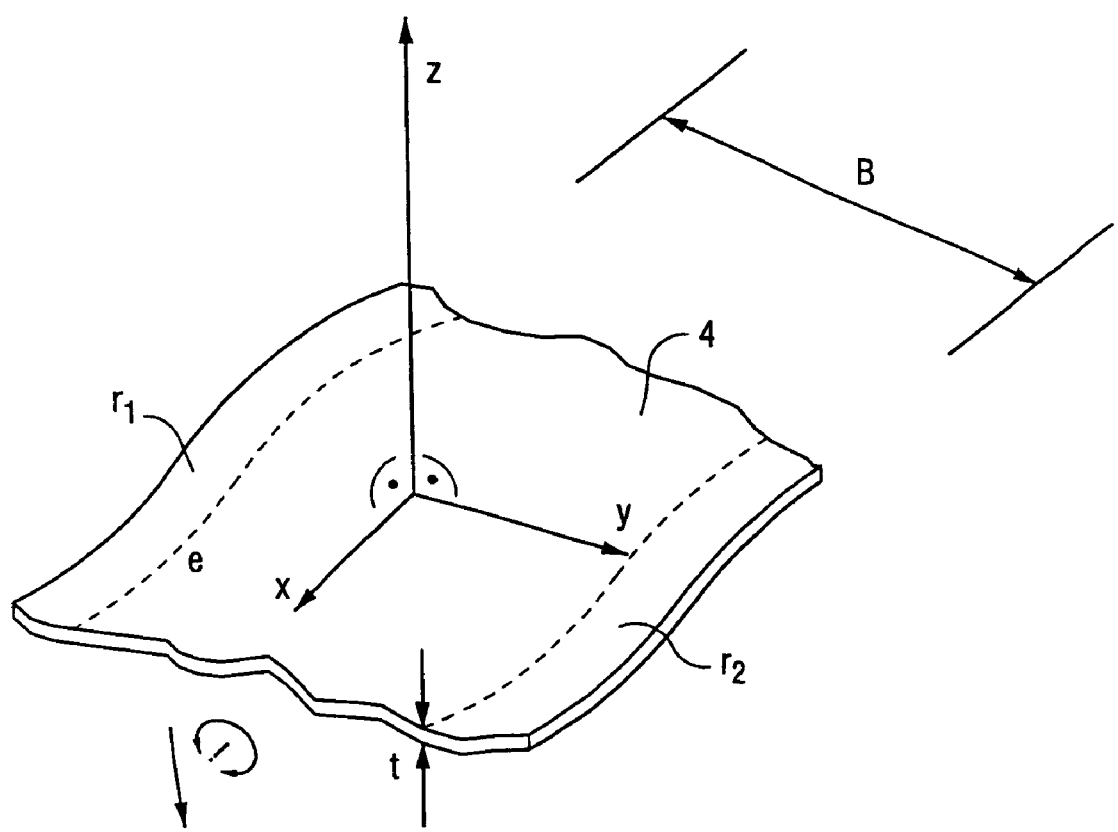
FIG. 11 is a principle sketch to explain the flexural strength of the flexible insert around their main axes.

FIG. 11 shows a basic sketch to explain the mechanical properties of the flexible reinforcement insert 4. The flexible reinforcement insert allows a bending strain around the main axes x and y extending in the main level e of the reinforcement insert 4. Deformations and reinforcement insert 4 around the main axis z extending perpendicularly to the level e are substantially avoided due to the large width of the reinforcement insert. The width B of the reinforcement insert 4 and the thickness t of the reinforcement insert 4 and the E-module E of the reinforcement insert 4 are preferably adapted such that the bending momentum around the main axis Z occurring during the application of the respiratory mask does not cause inadmissibly great deformations.

Since the flexural strength of the reinforcement layer 4 around the main axis Z is substantially defined by the edge zone portion r1, r2 of the reinforcement insert 4, it is possible to provide openings in the intermediate portion, so that the reinforcement insert 4 has a substantially latticework-like structure.

A latticework-like structure of the reinforcement insert 4 may in particular be realized in the manufacture of the reinforcement insert 4 by a plastic injection tool.

In zones of an especially high bending load it is also possible to provide a plurality of reinforcement inserts in the headband, or to form the reinforcement layers with locally thicker portions.

What is claimed is:

1. A holding device for a respiratory mask comprising:
a headband adapted to extend in an application position from a forehead portion of a patient around a back head portion of the patient;
a strengthening element releasably coupled to the headband to add flexural strength to the headband, the strengthening element being adapted to extend from the forehead portion laterally to respective ear portions and to descend behind the respective ear portions towards the patient's neck, the strengthening element having bracket sections positioned below respective ear portions adjacent the back head portion; and
a support coupled to respective bracket sections to support the bracket sections in the back head portion.

2. A holding device for a respiratory mask as claimed in claim 1, wherein the strengthening element has a section adapted to project towards the nose tip of the patient, which urges the respiratory mask against the face of the patient.

3. A holding device for a respiratory mask as claimed in claim 1, wherein the introduction of forces into the respiratory mask is performed in a manner that a deformation axis extends through a point of gravity which extends through a pressure distribution of a mask rest surface.

4. A holding device for a respiratory mask as claimed in claim 3, wherein the support defines a deformation axis that corresponds to the deformation axis acting on the mask.

5. A mask, comprising:
a headband;
a seal associated with a conduit having an opening at an upper end thereof, the opening being positioned above the seal and adapted to connect with an over-the-head type air delivery conduit;
a support frame extending from the headband to support the seal, the support frame including an upper end and a U-shaped lower end, the support frame including lateral portions spaced apart to define a gap that extends from the lower end to the upper end; and
a reinforcement element extending along at least part of the headband, the support frame being supported by the reinforcement element,
wherein the upper end of the conduit extends between the spaced lateral portions and within the gap.

6. A mask according to claim 5, wherein the support frame is adapted to exert a press-on force to force the seal into the patient's face in use.

7. A mask according to claim 5, wherein the headband is adapted to engage the patient in the application position from a forehead portion of the patient around a back head portion of the patient.

8. A holding device for a respiratory mask, comprising:
a pair of upper side band portions adapted to extend over the patient's ears;
an upper rear band portion adapted to extend along an upper portion of the patient's head, the upper rear band portion provided between the upper side band portions;
a pair of lower side band portions adapted to extend below the patient's ears;
a lower rear band portion adapted to extend along or adjacent a neck portion of the patient's head, the lower rear band portion provided between the lower side band portions;
a pair of connecting portions adapted to extend behind the patient's ears to interconnect the upper side band portions and upper rear band portion with the lower side band portions and lower rear band portion;
at least one of the band portions including a hook and loop fastener; and
at least one of the band portions having a multi-layered construction including a foam padding layer and a textile layer, the textile layer being provided between the foam padding layer and the patient's skin and adapted to contact the patient's skin.

9. A holding device according to claim 1, wherein the multi-layered construction includes an outer material layer adapted to face away from the patient's skin, the outer material layer constructed of a material adapted to adhesively connect with the hook and loop fastener.

10. A holding device according to claim 9, wherein the outer material layer is constructed of a fleece material.

11. A holding device according to claim 1, wherein the multi-layered construction includes a flexible reinforcement layer.

12. A holding device according to claim 11, wherein the flexible reinforcement layer is constructed of a thin spring sheet.

13. A holding device according to claim 12, wherein the flexible reinforcement layer is constructed of a thin spring steel sheet.

14. A holding device according to claim 11, wherein the flexible reinforcement layer is structured to allow the holding device to maintain its spatial shape.

15. A holding device according to claim 1, wherein the multi-layered construction includes a flexible reinforcement layer and an outer material layer constructed of a material adapted to adhesively connect with the hook and loop fastener, the flexible reinforcement layer provided between the outer material layer and the foam padding and textile layers.

16. A holding device according to claim 15, wherein the multi-layered construction includes a further foam padding layer between the outer material layer and the flexible reinforcement layer.

17. A holding device according to claim 1, wherein the multi-layered construction is formed by an ultrasonic welding process.

18. A holding device according to claim 1, wherein the multi-layered construction is formed by a flame backing process.

19. A respiratory mask, comprising:
a nasal-only seal; and
a holding device according to claim 1.

20. A holding device according to claim 1, wherein the multi-layered construction includes rounded lateral edges.

21. A holding device according to claim 1, wherein the multi-layered construction includes a patient contacting side having a generally convex exterior surface.

* * * * *